US 6,600,941 B1
Jul. 29, 2003

(12) United States Patent
Khuri

(10) Patent No.: US 6,600,941 B1
(45) Date of Patent: Jul. 29, 2003

(54) SYSTEMS AND METHODS OF PH TISSUE MONITORING

(75) Inventor: Shukri F. Khuri, Westwood, MA (US)

(73) Assignee: E-Monitors, Inc., Tewksbury, MA (US)

(*) Notice: Subject to any disclaimer, the term of this patent is extended or adjusted under 35 U.S.C. 154(b) by 0 days.

(21) Appl. No.: 09/580,809

(22) Filed: May 26, 2000

Related U.S. Application Data

(63) Continuation-in-part of application No. 09/339,081, filed on Jun. 23, 1999.
(60) Provisional application No. 60/136,502, filed on May 28, 1999.

(51) Int. Cl.[7] .................................................. A61R 5/00
(52) U.S. Cl. .......................... 600/345; 604/66; 604/67
(58) Field of Search ............................. 600/345–350, 600/18; 607/17–23, 65–67

(56) References Cited

U.S. PATENT DOCUMENTS

| | | | | |
|---|---|---|---|---|
| 3,973,555 A | 8/1976 | Möller et al. | ................... | 128/2 |
| 4,252,124 A | 2/1981 | Maurer et al. | ............... | 128/635 |
| 4,413,628 A | 11/1983 | Tamulis | ....................... | 128/635 |
| 4,467,807 A | 8/1984 | Bornzin | ...................... | 128/419 |
| 4,717,548 A | 1/1988 | Lee | .............................. | 422/68 |
| 4,774,956 A | 10/1988 | Kruse et al. | ................. | 128/635 |
| 4,912,417 A | 3/1990 | Gibboney et al. | ........... | 324/438 |
| 5,051,352 A | 9/1991 | Martindale et al. | ............ | 435/1 |
| 5,063,930 A | 11/1991 | Nucci | ........................ | 128/632 |
| 5,256,660 A | 10/1993 | Swan | ...................... | 514/238.8 |
| 5,304,495 A | 4/1994 | Yim | ............................ | 436/68 |
| 5,325,709 A | 7/1994 | Lee | ............................ | 73/61.43 |
| 5,472,876 A | 12/1995 | Fahy | ....................... | 435/284.1 |
| 5,522,389 A | 6/1996 | Fischer et al. | ............... | 128/634 |
| 5,533,971 A | 7/1996 | Phipps | ........................ | 604/20 |
| 5,603,817 A | 2/1997 | Settler et al. | ................ | 204/433 |
| 5,753,207 A | 5/1998 | Zuo et al. | ................... | 424/9.36 |
| 5,766,432 A | 6/1998 | Dunn et al. | .................. | 204/412 |
| 5,788,631 A | 8/1998 | Fiddian-Green | ............ | 600/309 |
| 5,813,403 A * | 9/1998 | Soller et al. | ................. | 600/322 |
| 6,090,096 A * | 7/2000 | St. Goar et al. | .............. | 600/18 |

FOREIGN PATENT DOCUMENTS

| | | |
|---|---|---|
| CA | 2151579 | 12/1995 |
| DE | 24 48 459 | 4/1975 |
| DE | 32 43 094 A1 | 5/1983 |
| EP | 0 354 719 A1 | 2/1990 |
| EP | 0 522 727 A1 | 1/1993 |
| FR | 2.198.638 | 9/1972 |
| FR | 2 744 804 | 8/1997 |
| GB | 2 045 940 | 11/1980 |
| JP | 08-182665 | 7/1996 |
| NL | 7415486 | 5/1976 |
| WO | WO 92/19150 | 11/1992 |
| WO | WO 98/26709 | 6/1998 |

OTHER PUBLICATIONS

Khuri, Shukri F., et al., "The Significance of the Late Fall in Myocardial Pco$_2$ and Its Relationship to Myocardial pH after Regional Coronary Occlusion in the Dog," Circulation Research, 56:537–547 (1985).
Reifart, Nicholas, MD, et al., "Effects of Bepridil on Regional Myocardial Ischemia and Comparison with Verapamil," The American Journal of Cardiology, 58:541–546 (1986).

(List continued on next page.)

Primary Examiner—Robert L. Nasser
(74) Attorney, Agent, or Firm—Bowditch & Dewey, LLP

(57) ABSTRACT

The invention relates to the use of pH measurements of tissue as a system for controlling diagnostic and/or surgical procedures. The invention also relates to an apparatus used to perform tissue pH measurements. Real time tissue pH measurements can be used as a method to determine ischemic segments of the tissue and provide the user with courses of conduct during and after a surgical procedure. When ischemia is found to be present in a tissue, a user can effect an optimal delivery of preservation fluids to the site of interest and/or effect a change in the conduct of the procedure to raise the pH of the site.

27 Claims, 8 Drawing Sheets

OTHER PUBLICATIONS

Lange, Rüdiger, M.D., et al., "Time Course of Ischemic Alternations During Normothermic and Hypothermic Arrest and Its Reflection by On–Line Monitoring of Tissue pH," Journal of Thoracic Cardiovascular Surgery, 86:418–434 (1983).

Randolph, John D., M.D., et al., "Improved Myocardial Preservation With Oxygenated Cardioplegic Solutions as Reflected by On–Line Monitoring of Intramyocardial pH During Arrest," Journal of Vascular Surgery, 3:216–225 (1986).

Khuri, Shukri F., M.D., et al., "First Report of Intramyocardial pH in Man: I. Methodology and Initial Results," Medical Instrumentation, 18:167–171 (1984).

Khuri, Shukri F., M.D., and Marston, William A. B.Sc., "On–Line Metabolic Monitoring of the Heart During Cardiac Surgery," Symposium on the Latest Advances in Cardiac Surgery, pp. 439–453, No date given.

Khuri, Shukri F., and Warner, Kenneth G., "Intraoperative pH Monitoring for the Detection of Progressive Myocardial Ischemia," Myocardial Protection in Cardiac Surgery, Brockton/West Roxbury Veterans Administration Medical Center–Harvard Medical School, West Roxbury, MA, pp. 399–412 (1987).

Khuri, Shukri F., MD, "Myocardial Protection During Reoperative Valve Surgery," A Textbook of Cardoplegia for Difficult Clinical Problems, 21:221–235 (1992).

Khuri, Shukri F., et al., "Changes in Intramyocardial ST Segment Voltage and Gas Tensions with Regional Myocardial Ischemia in the Dog," Circulation Research, 37:455–463 (1975).

Khuri, Shukri F., et al., "Intramural $Pco_2$: a reliable index of the severity of myocardial ischemic injury," American Journal Physiol., 237(2):H253–H259 (1979).

Alam, S., et al., "Lack of Effect of Nitroglycerin on the Transmural Variation of Tissue pH During Fixed Coronary Stenosis," Z. Kardiol., 72, 000–000 (1983).

Siouffi, Samer Y., et al., "Methods for the Metabolic Quantification of Regional Myocardial Ischemica," Journal of Surgical Research, 43:360–378 (1987).

Warner, Kenneth G., et al., "Significance of the Transmural Diminution in Regional Hydrogen Ion Production After Repeated Coronary Artery Occlusions," Circulation Research, 64:616–628 (1989).

Khuri, Shukri F., et al., "Metabolic Correlates of Myocardial Stunning and the Effect of Cardiopulmonary Bypass," Journal of Cardiac Surgery, 8:262–270 (1993).

Khabbaz, Kamal R., et al., "Simultaneous In Vivo Measurements of Intracellular and Extracellular Myocardial pH During Repeated Episodes of Ischemia," Current Surgery, 46:399–400 (1989).

Axford, Trevor, C., et al., "Electrod–derived myocardial pH measurements refelct intracellular myocardial metabolism assessed by phosphorus 31—nuclear magnetic resonance spectroscopy during normothermic ischemica," Journal of Thoracic and Cardiovascular Surgery, 103:902–907 (1992).

Zankoul, Fuad E., et al., "Time Course and Significance of Myocardial Tissue Acidosis During Global Ischemia and Sanguineous Reperfusion in the Isolated Rabbit Heart," Surgical Forum, 48:353–355 (1997).

Lange, Ruediger, et al., "Intramyocardial pH Measurement: A Useful Tool for the On–Line Assessment of Ischemic Damage and the Adequacy of Myocardial Preservation During Open Hear Surgery?," American College of Surgeons, Surgical Forum 33:290–292 (1982).

Lange, Rüdiger, et al., "The relative importance of alkalinity, temperature, and the washout effect of bicarbonate–buffered, multidose cardioplegic solution," Myocardial Protection, 70:I–75–I–83 (1984).

Khuri, Shukri F., et al., "The superiority of Continuous Cold Blood Cardioplegia in the Metabolic Protection of the Hypertrophied Human Heart," Journal of Thoracic and Cardiovascular Surgery, 95:442–454 (1998).

Warner, Kenneth G., et al., "Reduction in Myocardial Acidosis Using Blood Cardioplegia," Journal of Surgical Research, 45:247–256 (1987).

Warner, Kenneth G., et al., "Regional Changes in Myocardial Acid Production during Ischemic Arrest: A Comparison of Sanguineous and Asanguineous Cardioplegia," Annals of Thoracic Surgery, 45:75–81 (1988).

Dearani, Joseph A., et al., "Myocardial pH and Coronary Perfusion Pressure as Indicators of Survival During Cardiopulmonary Resuscitation," American College of Surgeons, Surgical Forum, 40:46–48 (1989).

Martin, David, et al., "The Effects of Normothermic and Hypothermic Cardiopulmonary Bypass on Defibrillation Energy Requirements and Transmyocardial Impedance," Journal of Thoracic and Cardiovascular Surgery, 109:981–988 (1995).

Khuri, Shukri F., et al., "First report of intramyocardial pH in man," Journal of Thoracic and Cardiovascular Surgery, 86:667–678 (1983).

Khuri, Shukri F., et al., "Observations on 100 patients with continuous intraoperative monitoring of intramyocardial pH," Journal of Throacic and Cardiovascular Surgery, 89:170–182 (1985).

Khuri, Shukri F., et al., "Intraoperative assessment of the physiologic significance of coronary stenosis in humans," Journal of Thoracic and Cardiovascular Surgery, 92:79–87 (1986).

Khuri, Shukri F., "Myocardial Preservation During Coronary Artery Bypass Surgery," Cardiac Surgery: State of the Art Reviews, 1:59–75 (1986).

Warner, Kenneth G., et al., "Metabolic and Microscopic Evidence of Ischemia in Valvular Heart Operation: Are we Really Protecting the Hypertrophied Ventricle?," American College of Surgeons, Surgical Forum, 36:216–218 (1985).

Warner, Kenneth G., et al., "Structural and Metabolic correlates of cell injury in the hypertrophied myocardium during valve replacement," Journal of Thoracic and Cardiovascular Surgery, 93:741–754 (1987).

Josa, Miguel, et al., "The Superiority of Blood Over Crystalloid Cardioplegia in Preventing Myocardial Acidosis During Global Cardiac Arrest," Cardiac Surgery, Surgical Forum, 253–255.

Dearani, Joseph A., et al., "Routine Measurement of Myocardial Temperature is Not Reflective of Myocardial Metabolism During Cardiac Surgery," American College of Surgeons, Surgical Forum, 41:228–230 (1990).

Khuri, Shukri F., et al., "Intraoperative Assessment of the Stunned versus Infarcted Myocardium with the Simultaneous Use of Transesophageal Echocardiography and the Measurement of Myocardial pH: Two Case Studies," Journal of Cardiac Surgery, 9:403–409 (1994).

Tantillo, Michael B., and Khuri, Shukri F., "Myocardial tissue pH in the assessment of the extent of myocardial ischemia and the adequacy of myocardial protection," Ischemia–reperfusion in cardiac surgery, 335–352 (1993).

Warner, Kenneth G., et al., "Comparative Response of Muscle and Subcutaneous Tissue pH During Arterial and Venous Occlusion in Musculocutaneous Flaps," Annals of Plastic Surgery, 22:108–116 (1989).

Kwasnik, Edward M., et al., "Hemodynamic and metabolic responses to graded microvascular occlusion," Journal of Vascular Surgery, 13:867–874 (1991).

Khuri, Shukri F., "Invited letter concerning: Changes in myocardial high–energy stores and carbohydrate metabolism during intermittent aortic crossclamping in dogs on cardiopulmonary bypass at 34° and 25° C," The Journal of Thoracic and Cardiovascular Surgery, 101:559–561 (1991).

Hassanein, W., et al., "Continuous Perfusion of Donor Hearts in the Beating State Extends Preservation Time and Improves Recovery of Function," *The Journal of Thoracic and Cardiovascular Surgery,* 116:821–830 (1998) XP002929772.

* cited by examiner

SYSTEMS AND METHODS OF PH TISSUE MONITORING

RELATED APPLICATION

This application is a continuation-in-part of U.S. application Ser. No. 09/339,081 filed on Jun. 23, 1999 which claims priority to US. Provisional Application No. 60/136,502 filed May 28, 1999, the entire teachings of the above applications being incorporated herein by reference.

BACKGROUND OF THE INVENTION

It is well known in the art to determine the pH in body fluids by using an electrode cell assembly and immersing the measuring electrode into a sample of the bodily fluid. The pH is known to be the symbol for the negative logarithm of the $H^+$ ion concentration. The pH value of the blood indicates the level of acidity of the blood. High blood acidity, which is reflected by a low pH indicates that the organs of the body are not being provided with enough oxygen, which can ultimately prove harmful.

It is also known in the art to measure tissue pH in myocardial tissue. Measurement of pH in myocardial tissue has been used to determine the presence of myocardial ischemia, as indicated by tissue acidosis which is reflected by a decrease in pH. During cardiac surgery, the aorta is cross clamped and the myocardium is deprived of its blood and nutrient supply, creating the potential for damage to the heart from ischemia. Ischemia can be diagnosed by monitoring the pH of the myocardium which falls significantly and becomes acidotic during ischemia.

There is an ongoing need, however, for further improvements in methods for diagnosing and treating ishemic tissue.

SUMMARY OF THE INVENTION

While ischemia or tissue acidosis, in cardiac tissue has been measured, systems and methods to prevent and/or reverse tissue, and in particular, cardiac acidosis were unknown. Surgeons did not know how to reverse tissue acidosis once discovered. The present invention relates to systems and/or methods of using tissue pH measurements to diagnose ischemia and to gauge the conduct of an operation, based on these pH measurements, so as to prevent and/or reverse tissue ischemia/acidosis. The current invention provides methods by which tissue acidosis can be corrected once discovered.

The present invention relates to pH-guided management of tissue ischemia or the use of pH measurements of tissue as a system for controlling diagnostic and/or surgical procedures. A preferred embodiment of the invention relates specifically to an apparatus and method which is applicable to patients undergoing cardiac surgery. It employs a tissue electrode and monitor and comprises a series of steps that, in a preferred embodiment, are aimed at achieving a homogeneous distribution of cardioplegic solution during aortic clamping, and at insuring adequate revascularization of ischemic segments of the myocardium. The method using pH-guided myocardial management guides the conduct of operations, prevents damage to the heart, extends the safe period of oxygen deprivation, and improves the outcome of patients undergoing heart surgery.

The use of the pH-guided myocardial management system to identify ischemic segments of a myocardium can provide a user with options for specific courses of conduct, both during and after, the surgical procedure. These options include: effecting an optimal delivery of preservation solutions to the heart to reduce ischemia, assessing the adequacy of coronary revascularization following a heart surgery procedure, identifying viable but nonfunctioning heart muscle, prompting changes in the conduct of the surgical procedure, monitoring the pH of the heart muscle post-operatively and evaluating the efficacy of newer myocardial protective agents.

There are several methods of delivery of a pH electrode, used in pH-guided myocardial management, to a site of interest. The electrode can be delivered manually by the user. The electrode can also be delivered by a catheter through a percutaneous incision. The electrode can also be delivered by an endoscope, a colonoscope or a laparoscope to a site of interest. Thus, in a preferred embodiment of the invention, the method can be applied to other tissue measurements such as brain tissue, kidney tissue, musculocutaneous flaps or the small or large intestines. In another embodiment, the pH of transplanted organs, such as liver or kidney, can be measured to assist in the diagnosis and/or treatment of rejection since acidosis is an early sign of rejection.

Other systems and methods can also be used to measure pH, including, in certain applications, surface pH measurements, magnetic resonance measurements, or optical methods using fiber optic probes or endoscopes.

When a user has found that tissue acidosis is present at a site of interest, the user can effect an optimal delivery of preservation fluids, or cardioplegia fluids, to the heart to raise the pH of the site. Several systems that provide optimal delivery of the cardioplegia solutions to the site are available to the user. These include: altering the flow rate of the preservation fluid, altering the temperature of the fluid, altering the site of delivery, repositioning the tip of the catheter, selectively directing the preservation fluid through the manifold, applying direct coronary artery pressure on the proximal portion of the artery, occluding the left main coronary artery with a balloon catheter, inflating the balloon of a retrograde coronary sinus catheter, administering a bolus of cardioplegia through the orifice of a right coronary artery and accelerating a surgical procedure.

When a user has found that tissue acidosis is present at a site of interest, the user can also prompt changes to the conduct of the surgical procedure to raise the pH of the site. Several alternatives for changing the surgical procedure are available to the user. These include: determining the need for revascularization of a specific segment of the myocardium, changing the order of revascularization, providing for additional revascularization, changing the operation or the surgeon to reduce ischemic time, canceling an operation and delaying the weaning of a patient from cardiopulmonary bypass.

The pH electrode itself can have a cable connected to a silver wire where the silver wire is an Ag/AgCl (silver/silver chloride) wire. The cable and wires are encased in a housing which is encased in shrink tubing. The electrode has a glass stem which houses the silver wire, a thermistor, a pH sensor, and a gelled electrolyte. The electrode has a bendable joint which allows the user to adjust the positioning of the electrode prior to or during use and which facilitates electrode removal after chronic insertion. The glass stem is pointed to allow direct insertion into tissues. In a preferred embodiment, the glass stem is made of lead glass.

The electrodes can be used in a probe that can be delivered to a site within the human body using a catheter and/or endoscope. The sensor can be connected to a data processing system such as a personal computer that can be used to record and process data. The computer can be programmed using a software module to control system operation and indicate to the user the status of the patient and changes in system status and operation. The system can also prompt the surgeon as to indicated changes in a surgical procedure in progress. The computer can be connected to a controller that operates a fluid delivery system and various temperature and pressure sensors can provide data for the monitoring system regarding patient status.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
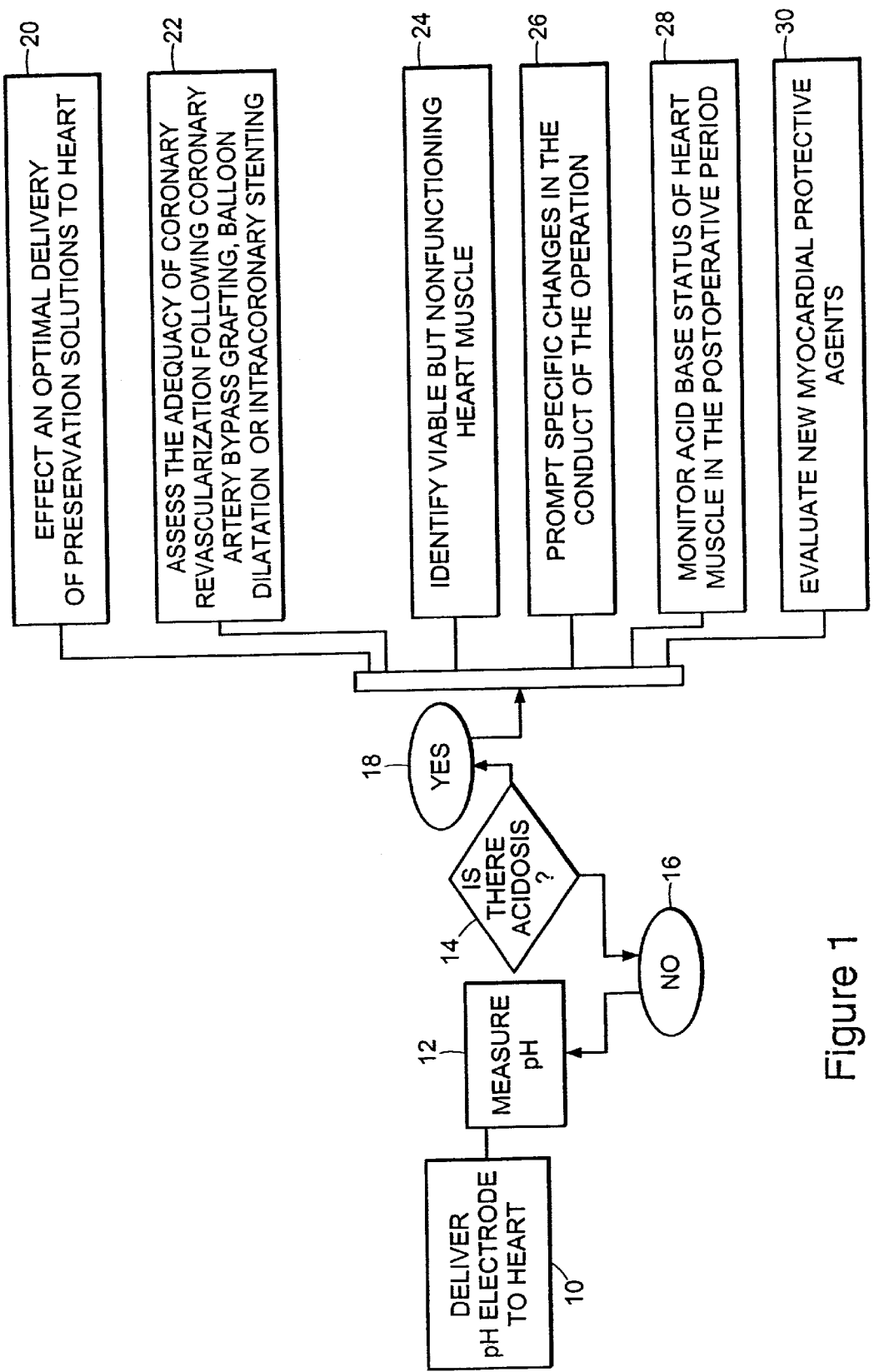
FIG. 1 illustrates a method of using tissue pH to identify ischemic segments of a myocardium and the options available to a user to utilize this information and take an appropriate course of action.

FIG. 1 illustrates a method of using tissue pH to identify ischemic segments of the heart, which are regions of the heart muscle that are not receiving an adequate blood and nutrient supply, and the options available to a user to take advantage of this information and pursue an appropriate course of action. A user would first deliver a pH electrode to a patient's heart 10. The user would then measure the tissue pH as displayed on a monitor 12 and determine whether or not there was acidosis present in the tissue 14. If there is no tissue acidosis 16, the pH would be again measured 12. In a preferred embodiment, the pH is continually measured by the electrode with the pH measurements displayed on a monitor. If acidosis existed in the tissue 18, however, the user could use this information to take appropriate action such as, but not limited to, the following:

A user can effect an optimal delivery of the preservation solutions to the heart through one or more of a compendium of specific interventions 20. To perform open heart surgery, the aorta has to be clamped thus depriving the heart muscle from its blood, nutrient, and oxygen supply. A preservation solution, often referred to as a cardioplegic solution, is normally perfused into the heart and its blood vessels to prevent time-dependent ischemic damage. It has been shown that the measurement of tissue pH, which reflects, in part, the washout of the hydrogen ion generated by the metabolic processes, is a good indicator of the regional distribution of the preservation solution. It has also been shown this distribution to be markedly heterogenous and unpredictable, with segments of the myocardial wall suffering from acidosis because of failure of the cardioplegic solution to reach these segments. The main objective of pH-guided myocardial management is to prevent tissue acidosis in all the segments of the myocardium throughout the course of open heart surgery. This is achieved by insuring an adequate and a homogeneous delivery of the cardioplegic solution and an adequate revascularization of ischemic segments of the heart. These are achieved by maintenance of the myocardial pH as near normal as possible, with normal pH ranging between 7.2 and 7.4.

A user can also assess the adequacy of coronary revascularization following coronary artery bypass grafting, balloon dilatation or intracoronary stenting 22. This functionality employs the rate of washout of the hydrogen ion accumulating in the tissues during ischemia as an indication of the magnitude of tissue blood flow. Following restoration of flow through a newly constructed aorto-coronary bypass graft, no change in the pH of a myocardial segment subtended by that graft indicates inadequate revascularization. On the other hand, a rise in the pH of more than 0.1 pH units indicates restoration of effective tissue flow to the ischemic myocardium.

A user can also identify viable but non-functioning heart muscle 24, known as hibernating myocardium, which improves its function with adequate coronary revascularization. pH-guided myocardial management has demonstrated that the ability of the non-contractile myocardial wall segment to produce acid, i.e. to exhibit tissue acidosis, is an indication of the viability and reversibility of dysfunction in this segment. Hence the procedure provides a tool with which the viability of the non-contractile myocardial segment can be assessed.

A user can also prompt specific changes in the conduct of the operation 26 after obtaining information regarding tissue pH. These changes in operating procedure are outlined in greater detail in FIG. 4.

A user can also monitor the acid-base status of the heart muscle in the post-operative period 28 and identify impending problems. This functionality allows the depiction of ischemic events in the intensive care unit within the first 72 hours postoperatively. This methodology is capable of continuous monitoring of regional tissue metabolism and acid base balance in a patient, post-surgery. A fall in the myocardial pH of more than 0.1 pH units in the face of a stable blood pH is indicative of myocardial ischemia. The more severe the fall in the pH the more the magnitude of the ischemic damage. This functionality is achieved by implanting the electrodes in the myocardium at the time of the operation and exteriorizing them through a special chest tube. The electrodes are pulled out in the surgical intensive care unit (SICU) after the monitoring is terminated by simply pulling on them along with the chest tube which houses them.

The user can also evaluate the efficacy of newer myocardial protective agents and methods in the prevention of tissue acidosis and the improvement of patient outcomes 30. To improve myocardial protection, a number of agents are being proposed as additions to the cardioplegic solution, and new modalities for the administration of cardioplegia are being sought. pH-guided myocardial management provides a metabolic marker which can enable the assessment of the efficacy of these new agents and modalities in improving the degree of intraoperative protection, the hallmark of which can be the degree of prevention of acidosis during the period of aortic clamping. The variable employed to compare these methods of myocardial protection is the integrated mean myocardial pH during the period of aortic clamping. The higher the integrated mean pH during this period, the better is the degree of myocardial protection.

Figure 2:
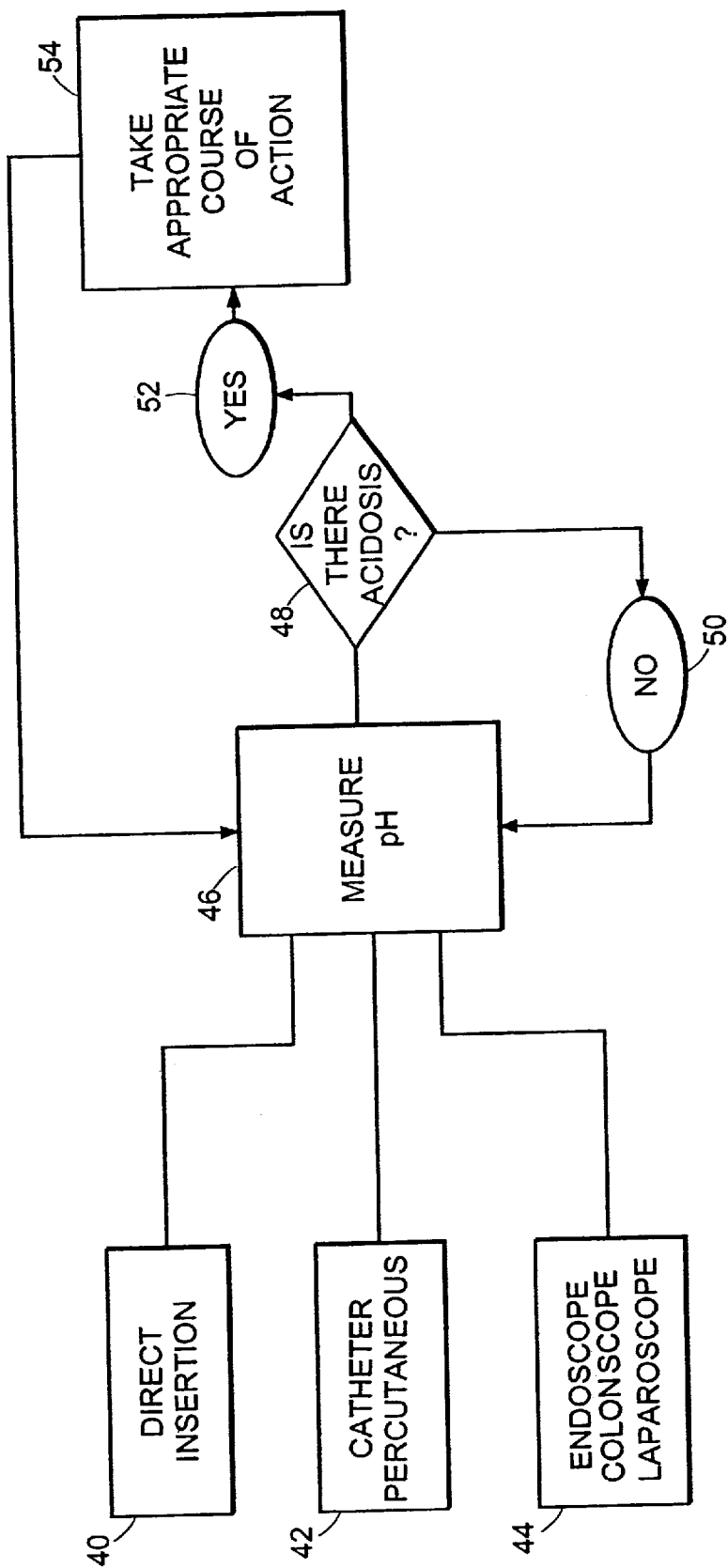
FIG. 2 illustrates the methods of delivery of a pH electrode to cardiac tissue.

FIG. 2 illustrates various methods of delivery of a pH electrode to cardiac tissue. A user can implant the pH electrode using direct insertion 40. This can include opening the chest cavity of a patient during a cardiac surgery procedure and placing the electrode into the patient's cardiac tissue by hand. The user can also insert the pH electrode by means of a catheter using a percutaneous incision 42. A user can also insert the pH electrode by using an endoscope, colonscope or laparoscope 44. The user can then measure the pH of the tissue 46 and determine whether there is acidosis in the tissue 48. If no acidosis is found 50, the pH of the tissue can again be measured 46. If acidosis is found in the tissue 52, the user can then take an appropriate course of action 54, as outlined in FIG. 1.

Figure 3:
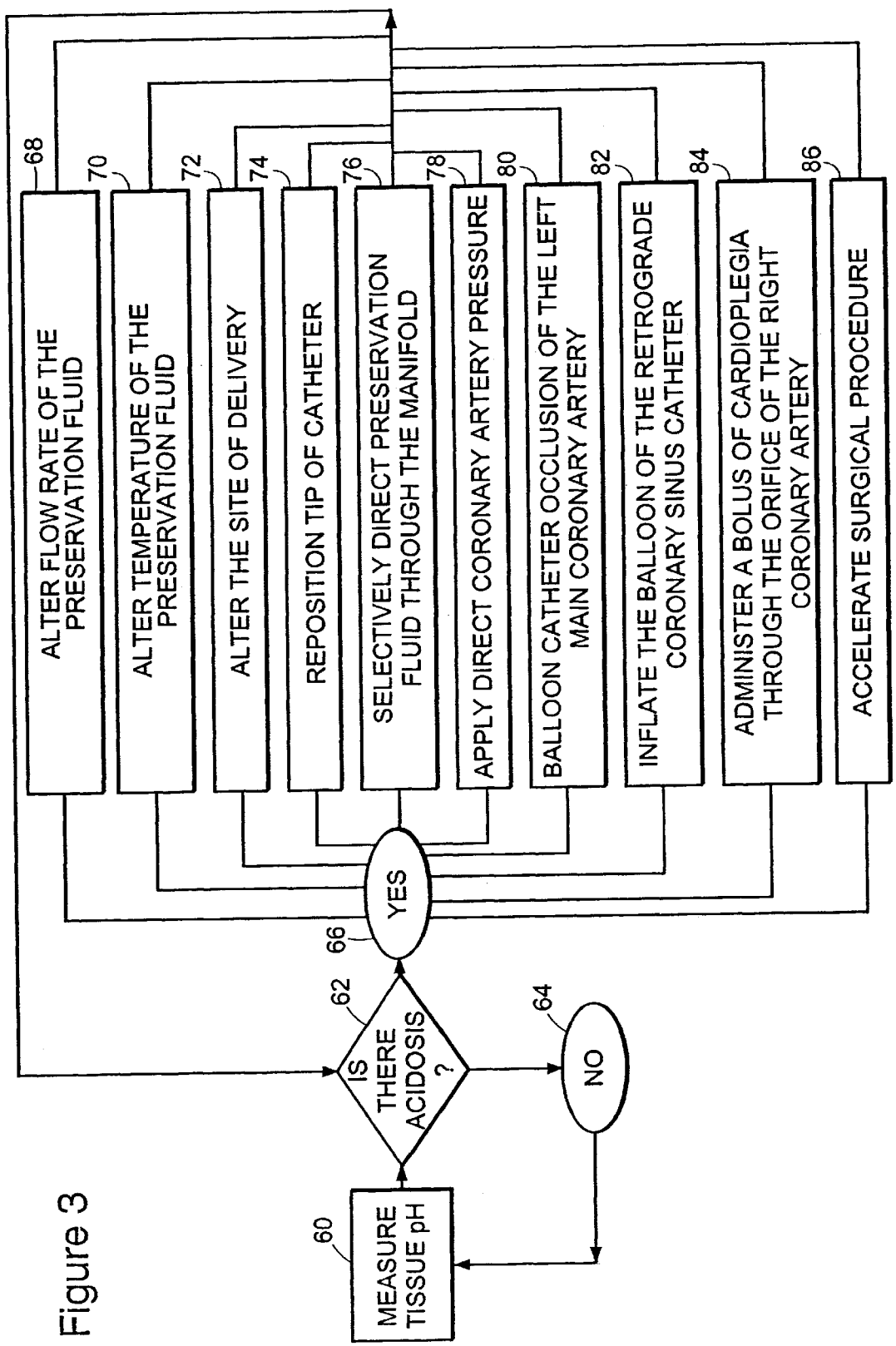
FIG. 3 illustrates a method of effecting an optimal delivery of preservation solution to the heart during surgery.

FIG. 3 illustrates a method of providing for an optimal delivery of preservation solution to a heart during surgery. In this method, a user can first measure cardiac tissue pH 60 and determine whether there is acidosis in the tissue 62. If no acidosis is found 64, the pH of the tissue can again be measured 62. In a preferred embodiment, the pH is continuously measured and monitored. If acidosis is found in the tissue 66, the user can then effect an optimal delivery of the preservation solutions to the heart through one or more of a compendium of specific interventions. Interventions to be used to effect an adequate and a homogeneous delivery of the cardioplegic solution include, but are not limited to, the following maneuvers:

The user can alter the flow rate of the preservation solution 68 to provide an optimal delivery of the cardioplegia solution. The perfusionist controls the flow rate of the cardioplegic solution administered. pH-guided myocardial management has demonstrated that patients and myocardial segments differ in the flow rate necessary to prevent acidosis. Therefore, changing the flow rate of the cardioplegia solution can alter and improve tissue pH.

The user can also alter the temperature of the preservation solution 70 to optimize solution delivery. Changes in myocardial temperature, which can range widely in the course of cardiac surgery, effect various degrees of vasoconstriction and vasodilatation of the coronary vasculature. This, in turn, will effect the distribution of the cardioplegic solution and also the level of tissue acidosis. Avoidance of tissue acidosis can be achieved either by cooling or by re-warming the cardioplegic solution, depending on the effect of temperature on the regional distribution of the cardioplegic solution. pH-guided myocardial management has demonstrated that the effect of temperature on the regional distribution of the cardioplegic solution is totally unpredictable and, hence, continuous monitoring of myocardial tissue pH allows the determination of the myocardial temperature which is most likely to prevent myocardial acidosis. Opposite effects on myocardial pH have been observed from patient to patient with both cooling and rewarming. In general, however, giving warm cardioplegia effected an improvement in tissue pH in most patients.

To provide an optimal delivery of the solution, the user can also alter the site of delivery of the cardioplegic solution 72. The cardioplegic solution can be delivered through several sites: antegrade through the aortic root, antegrade through the orifice of the right and/or left main coronary arteries, antegrade through the proximal ends of newly constructed grafts, and retrograde through the coronary sinus. pH-guided myocardial management allows the surgeon to choose the site or combination of sites of administration which can best avoid regional acidosis.

The user can reposition the tip of the catheter through which the cardioplegic solution is delivered 74 to optimize delivery. This may need to be performed in patients with a very short left main coronary artery when cardioplegia is administered through the orifice of the left main. It can also be useful in pulling back on a retrograde catheter which is pushed too far into the coronary sinus.

The user can also selectively direct the cardioplegic solution through a manifold so as to reduce the steal of the solution 76. The cardioplegic solution can be delivered through a manifold having several catheters radiating from a single source. This arrangement of the manifold is known as a "turkey foot". When the cardioplegic solution is administered through more than one of these catheters simultaneously, there is a marked heterogeneity in the distribution of the solution to the various myocardial segments supplied by these catheters. The solution often moves preferentially into the catheter supplying the myocardial segment with least resistance, usually the myocardial segment with least coronary artery disease. This is what is referred to as a "steal phenomenon." Monitoring myocardial pH, which capitalizes on the fact that the rate of washout of the hydrogen ion in tissue is indicative of the magnitude of tissue flow, can determine which segments of the myocardium are receiving the cardioplegic solution and which segments are deprived of cardioplegia because of the "steal" phenomenon. When steal is encountered, homogeneity of the distribution of the cardioplegic solution can be achieved by occluding the catheters responsible for the steal and by specifically directing the flow only into the areas exhibiting acidosis.

The user can also apply direct coronary artery pressure on the proximal portion of the artery to distally direct cardioplegia flow through a newly constructed graft 78. This pressure can force the cardioplegia solution to an area with low pH, to lower tissue acidosis in that area.

The user can perform a balloon catheter occlusion of the orifice of the left main coronary artery during the delivery of retrograde cardioplegia through the coronary sinus or through the proximal ends of recently constructed saphenous vein grafts 80. The balloon catheter occlusion of the left main coronary artery prevents the steal phenomenon, where the solution follows the path of least resistance, and forces the cardioplegia solution to an area of low pH. This process can reverse acidosis of an area showing a low pH.

The user can also inflate the balloon of a retrograde coronary sinus catheter while the cardioplegic solution is being administered antegrade 82. Normally, if cardioplegia is being delivered antegrade and retrograde simultaneously, the balloon in the coronary sinus is kept deflated. A more homogeneous distribution of the cardioplegic solution can be achieved if the balloon in the coronary sinus is kept inflated while the cardioplegia is delivered simultaneously antegrade and retrograde.

The user can also administer a bolus of cardioplegia through the orifice of the right coronary artery when the latter is a dominant, non-obstructed vessel 84. In the course of an open heart operation in which the aortic root is open, cardioplegia can be administered through the orifice of the right coronary artery in addition to the orifice of the left coronary artery. This, however, can be tedious and time consuming, hence it is not a common practice. pH-guided myocardial management has shown that the posterior left ventricular wall is more vulnerable to refractory myocardial acidosis if the right coronary artery is dominant and no cardioplegia is administered through it. Hence, if in the course of pH-guided myocardial management, refractory acidosis is encountered in the posterior wall, administering a bolus of cardioplegia through the orifice of the right coronary artery, if the latter is dominant, can insure adequate delivery of the cardioplegic solution to the posterior wall and can reverse the acidosis.

A user can also accelerate the surgical procedure 86 when tissue acidosis is present. By monitoring tissue acidosis, a user can avoid either using his time wastefully or attempting nonstandard or potentially ineffectual surgical procedures. Also, in few patients, less than 5%, there is no known method to prevent tissue acidosis and the surgical procedure must be accelerated. With the acceleration of a procedure, the aorta, which is clamped during the surgery, is unclamped sooner than planned, thus allowing oxygen rich blood to reach the heart muscle, thereby reversing acidosis.

In the event that one of the described options, 68 through 86, fails to relieve the ischemic condition, as evidenced by the display of tissue pH levels on the pH monitor, the user can use any of the other described options to attempt to raise tissue pH.

Figure 4:
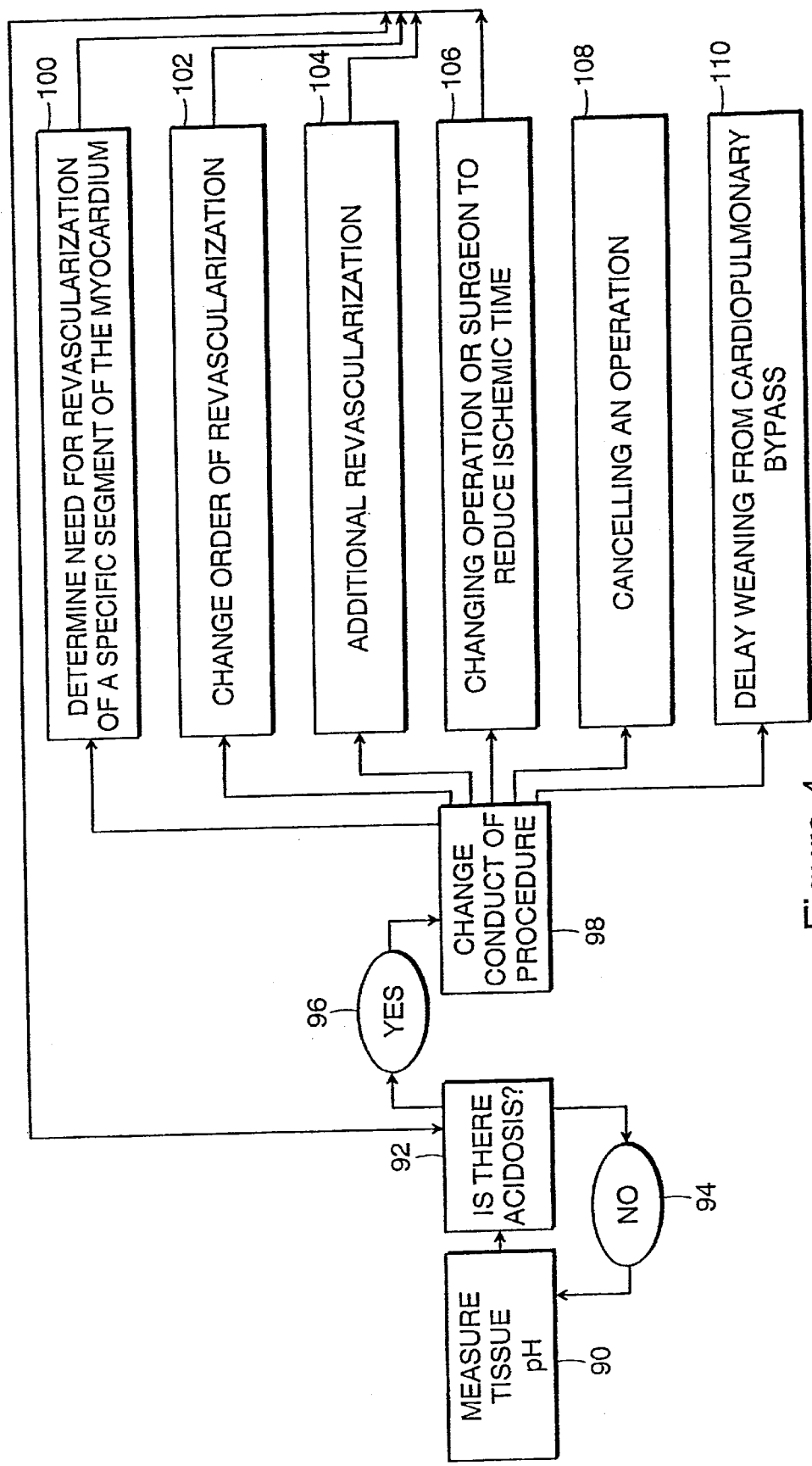
FIG. 4 illustrates a method of using the pH electrode to measure the condition of tissue and alter the conduct of an operation involving the tissue.

FIG. 4 illustrates a method of using the pH electrode to prompt specific changes in the conduct of an operation after determining there is tissue acidosis. In this method, a user first measures cardiac tissue pH 90 and determine whether there is acidosis in the tissue 92. If no acidosis is found 94, the pH of the tissue can again be continuously or periodically measured 90. If acidosis is found in the tissue 96, the user can then change the conduct of the procedure 98.

These changes can include, but are not limited to, the following maneuvers. First, the determination of the need for the revascularization of a specific segment of myocardium 100. The ability to identify which specifically are the segments of the myocardium that need revascularization can be lifesaving. Segments requiring revascularization can be determined by either examining the onset of regional acidosis in the course of an operation or the response of the myocardial pH to atrial pacing. The response to atrial pacing can be utilized intra-operatively, postoperatively in the SICU, and in the cardiac catheterization laboratory.

The user can also change the order of revascularization. pH-guided myocardial management allows the surgeon to revascularize the most ischemic segments of the myocardium first so as to minimize the degree of acidosis encountered in the course of aortic clamping.

The user can also change the procedure by providing additional revascularization of the heart 104. pH-guided myocardial management involves identifying ischemic segments of the left ventricular wall that require revascularization, often unplanned preoperatively.

The user can also change the operation or the surgeon to reduce the duration of the ischemic time 106. pH-guided myocardial management allows for reductions in the magnitude of the planned operation in several ways. When pH monitoring depicts a significant amount of myocardial acidosis which cannot be corrected, the need to reduce the ischemic time becomes more important than the potential benefits of certain parts of the operation that can be dispensed with, such as the construction of an additional graft. pH monitoring also allows the surgeon to abandon a planned part of the operation because it uncovers no real need for this part. In this context, pH-guided myocardial management also plays a major value in the teaching of residents because it provides the attending surgeon with the information on what parts of the operation he/she can give to the resident, and what part the attending surgeon can be doing himself/ herself, since residents, particularly early in their training, can be fairly tardy in performing these operations.

The user can also cancel an operation 108 if, based on the pH measurements, the risk of the procedure is found to exceed the benefit.

Lastly, the user can delay the weaning from cardiopulmonary bypass until the oxygen debt, represented by residual acidosis during reperfusion, is fully paid 110. Weaning from cardiopulmonary bypass in the presence of myocardial acidosis may cause the hemodynamics to deteriorate postoperatively, often prompting the re-institution of cardiopulmonary bypass. When the heart is subjected to significant ischemia during the period of aortic clamping or reperfusion, a significant amount of time may be needed until the ischemia reverses to normal levels.

In the event that one of the described options, 100 through 106, fails to relieve the ischemic condition, as evidenced by the display of tissue pH levels on the pH monitor, the user can use any of these other described options to attempt to raise tissue pH.

Figure 5:
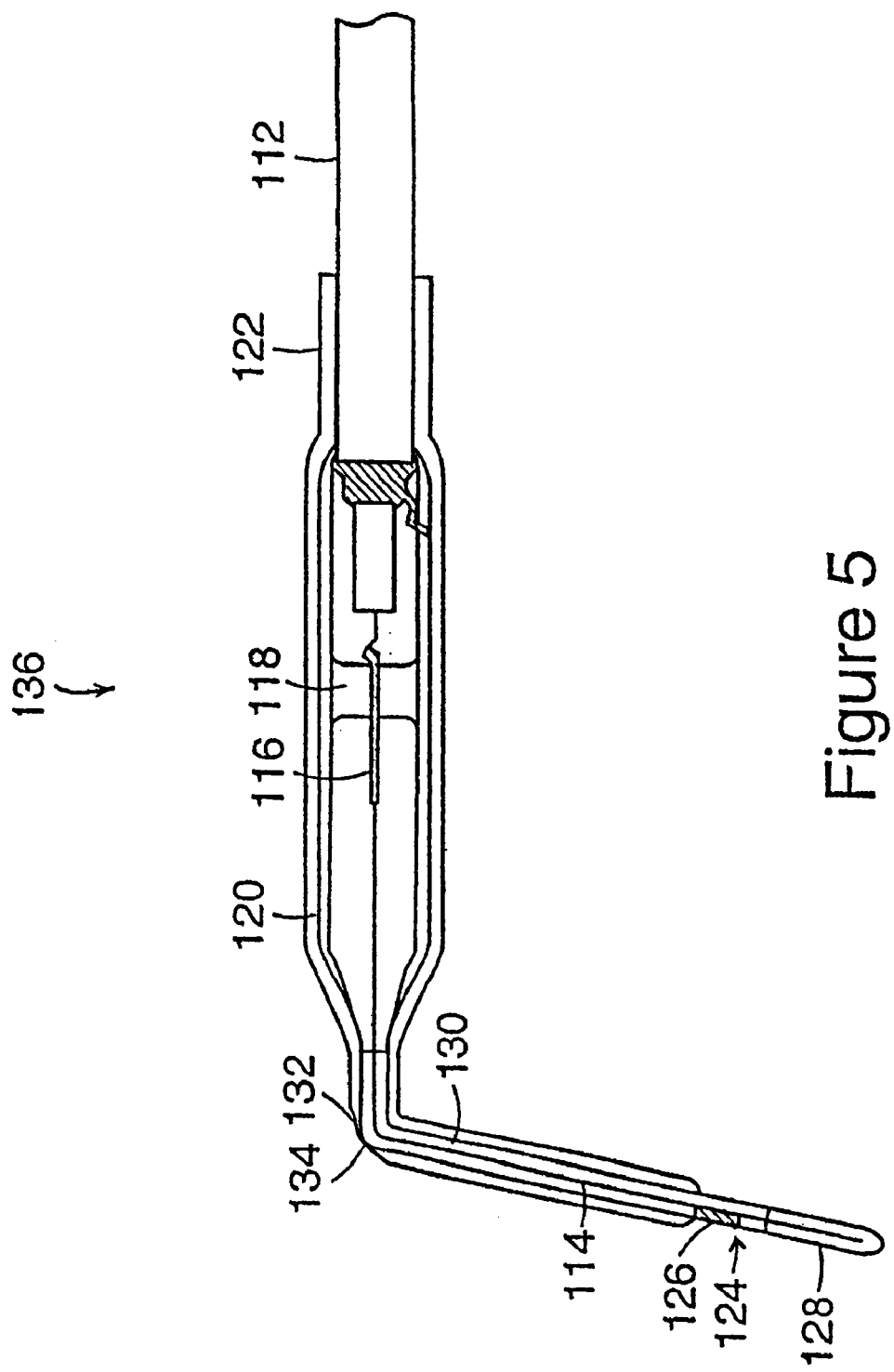
FIG. 5 illustrates a sectional view of an embodiment of a pH electrode.

FIG. 5 illustrates an embodiment of a pH electrode 136 used to monitor tissue acidosis. The electrode 136 can have a cable 112 connected to a silver wire 114. In a preferred embodiment, the silver wire 114 is an Ag/AgCl (silver/silver chloride) wire. In another preferred embodiment, the cable 112 is connected to the silver wire 114 by a platinum wire 116 passing through a glass seal 118. The cable 112 and wires 114, 116 are encased in a housing 120 which is encased in shrink tubing 122. The electrode 136 has a glass stem 124 which houses the silver wire 114, a thermistor 126, a pH sensor 128, and a gelled electrolyte 130. The electrode 136 can also have a suture groove 132 to allow the electrode 136 to be secured to the site where it is used. The electrode 136 can also have a bendable joint 134 which allows the user to adjust the positioning of the electrode 136 prior to or during use. The glass stem 124 is pointed to allow direct insertion into tissues. In a preferred embodiment, the glass stem 124 is made of lead glass. The electrode can be sterilized by ethylene oxide or gamma irradiation. A pH electrode suitable for use with the invention is available from Vascular Technology Inc., 175 Cabot Street, Lowell, Mass. This particular electrode can be inserted into tissue to a depth of up to 10 mm, has a diameter of 1 mm, and employs a pH sensor in the distal 4 mm of the probe.

Tissue pH is an important clinical measurement. Local acidosis, which can be measured as a distinct drop in pH, has been associated with ischemia. Temperature is preferably measured simultaneously with the pH to allow for the calibration and temperature correction of the tissue pH measurement. Temperature correction of the pH is important, particularly in procedures, such as open-heart surgery, which require significant cooling. The pH electrode uses combination pH/temperature sensors, each of which contains a temperature-sensing element mounted inside the pH-sensing sensor.

Glass pH electrodes are the method most commonly used to obtain accurate clinical pH measurements. They consist of a hollow glass sensor filled with electrolyte that is in turn in contact with an internal reference wire. Due to the nature of the glass used, an electric potential is developed across the glass. This potential is proportional to the difference between the pH of the analyte solution in contact with the exterior surface of the glass and the essentially constant pH of the internal buffer solution.

In order to make an electrical measurement, a complete electric circuit must be formed. Therefore, a second electrical contact with the analyte solution must be made. This is accomplished through the use of a needle reference electrode. It consists of a silver chloride needle in contact with a constant molarity salt solution. The salt solution is placed in contact with the analyte solution, i.e., the patient's tissue, using a suitable isolation mechanism, in this case through the use of gelled salt solution that has been placed in a flexible tube, the open end of which is placed in contact with the patient.

The Nernst equation predicts that under constant environmental conditions, the output of the glass pH electrode is linear with pH. Therefore, the electrical output of the sensor can be converted to pH by the use of a simple straight-line curve-fit. This will require determining the electrical output of the electrode at two different pH values, from which the slope and offset constants for the straight-line equation can be calculated. The commonly available standards buffers for pH electrode calibration have pH values of 4, 7, and 10. The 4 and 7 buffers have been chosen for use with this system. The 7-pH buffer was chosen because the electrode's zero-potential point is near pH 7. The 4-buffer was chosen because pH values of the greatest interest lie somewhat below pH 7.

The theoretical sensitivity-the slope-of this type of electrode is 59.16 mV/pH at 25° C. For real electrodes, it tends to be a little less, the value being slightly different from one electrode to another and, for a given electrode, varying over its useful life.

The zero potential point is defined, as that analyte pH value for which the measured output voltage is zero, after correcting for any difference in the salt concentrations of the internal and reference solutions. The zero potential point should occur, therefore, when the analyte pH value is the same as the pH value of the pH sensor's internal buffer. If a measurement is actually made under these conditions, however, a non-zero potential will, in general, be measured. This occurs when the CI connection that the sensor's internal reference wire is exposed to differs from the concentration that the reference needle is exposed to, or if both reference wires are not made of the same material. In this system, the reference needle is immersed in a saturated KCl gel, while the sensor's internal reference wire is exposed to an 0.87M concentration of KCl in the internal buffer. This difference results in a measured potential of about +30 mV at 25° C. when the analyte has the same pH value as that of the internal buffers, nominally 6.33 pH at 25° C. Thus, in order to measure the true zero potential point, it is necessary to correct the measured voltage by subtracting 30 mV from it. The pH 7 buffer is used during calibration for zero point calibration is the closest readily available buffer value to 6.33.

Since there is some variation in output from the ideal values as just described, both from sensor to sensor and over extended periods of time for the same sensor, the pH sensors must be calibrated prior to each use. This is accomplished automatically during the calibration procedure by placing the sensors first in the slope buffer (4.00 pH) and then in the zero potential point buffer (7.00 pH). The microprocessor reads the output of the sensors in mV, correcting for the salt differential, determines when the readings are stable and then computes the slope and offset calibration factors for each sensor. Both the slope and zero potential point vary with temperature and are corrected for by the monitor's software.

The pH electrode's combination pH/temperature sensor uses a precision thermistor element to measure temperature. The thermistor is one of the most common temperature measuring devices in use. It consists of a small bead of metallic oxide semiconducting ceramic. The material's electrical resistance varies inversely with temperature in a non-linear manner.

To measure temperature, the thermistor is electrically placed in series with a fixed resistor in the monitor that has precisely known resistance. A voltage is applied across the series combination and the voltage at the junction of the thermistor and resistor is measured. This measured value, in conjunction with the known values of the fixed resistor and of the applied voltage, is used to calculate the resistance of the thermistor. The temperature is then determined by means of a look-up table stored in the microprocessor program. The thermistor sensors used with this system are manufactured to a level of precision that makes individual calibration by the user of the system unnecessary.

The pH electrode can be pre-calibrated and packaged such that the tip of the electrode is sealed within a sleeve or a sleeve pocket containing a pH 4.0 buffer. The sleeve pocket can be formed of a plastic material and can have a 3 mm internal diameter. Prior to its insertion in the patient, the sleeve pocket can be removed, the electrode tip wiped dry with a gauze, and the electrode inserted into a beaker containing a pH 7.0 buffer. The calibration is completed at this point. Packaging the electrode within a pH 4.0 buffer allows the electrode to remain moist through its storage, a factor which is necessary for proper calibration, and reduces the steps required for electrode calibration to a single step. The software in the electrode monitor can be modified to reflect the single step calibration.

The monitor, to which the pH electrode, the reference electrode, and thermistor are attached, processes the signals and continually records and displays the following data at 20 second intervals or less: 1) the tissue pH in pH units, 2) the tissue hydrogen ion concentration [$H^+$] in nmoles, 3) the tissue temperature in ° C., 4) the pH corrected for 37° C., and 5) the tissue hydrogen ion concentration [$H^+$] is calculated as the inverse log of pH. The correction for 37° C. is based on a factor of 0.017 pH units /° C. which was derived based on experiments performed in the inventor's laboratory. In addition, the monitor allows for the calculation of integrated mean pH, [$H^+$], and temperature over a specific period of time by signaling at the beginning and at the end of the specified period. A slave monitor is attached to the unit and placed in front of the surgeon providing a customized continuous display of the data. The continuous real-time display of the data allows for prompt institution of pH-guided myocardial management to prevent or reverse myocardial tissue acidosis.

Several devices or tools can be used in pH guided myocardial management during cardiac surgery and in the assessment of myocardial viability. The maintenance and distribution of cardioplegic solution to specific myocardial segments during cardiac surgery can be achieved using several different devices and approaches.

Figure 6:
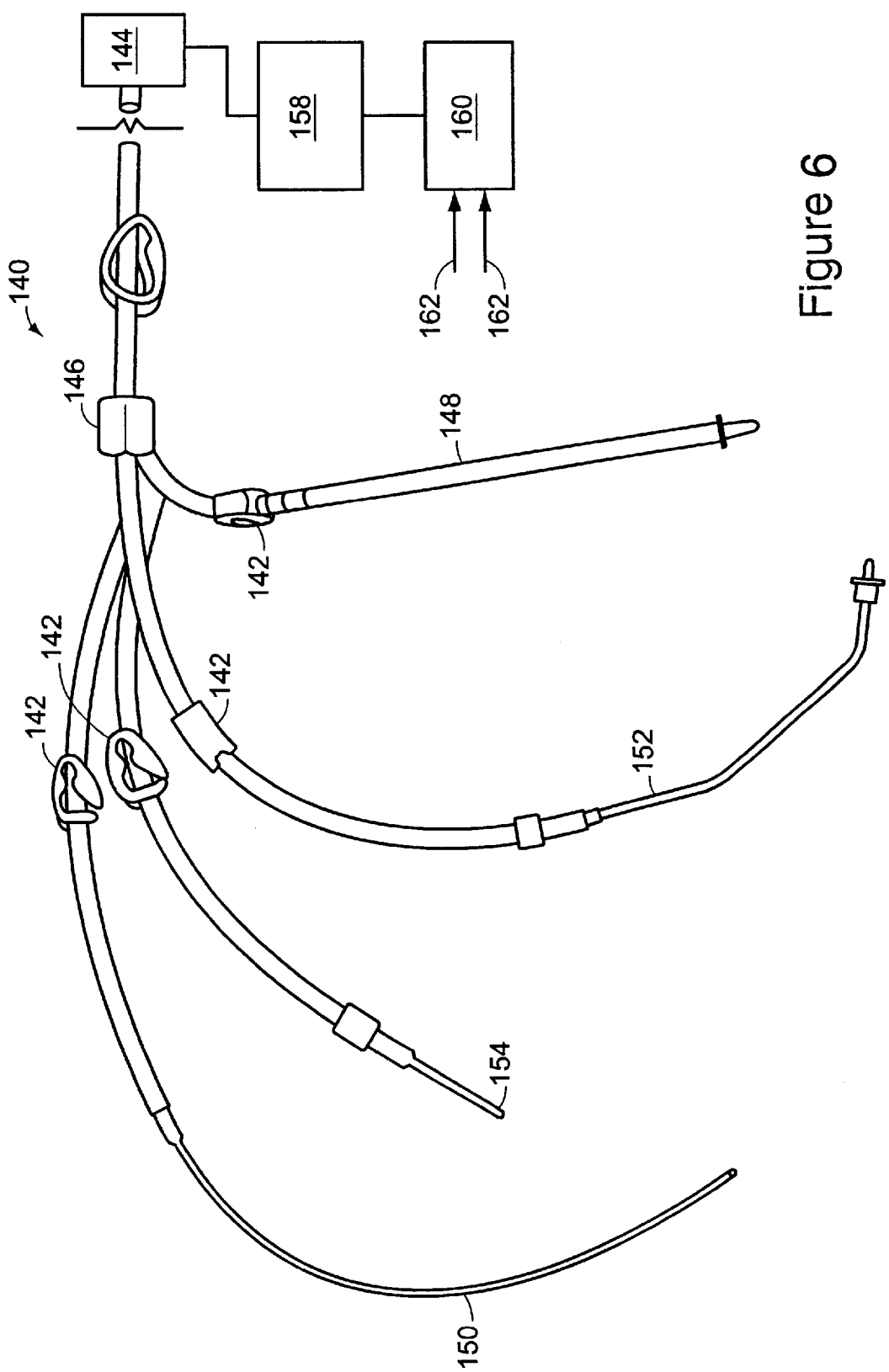
FIG. 6 illustrates a turkey foot cardioplegia delivery system and tools.
Figure 7A:
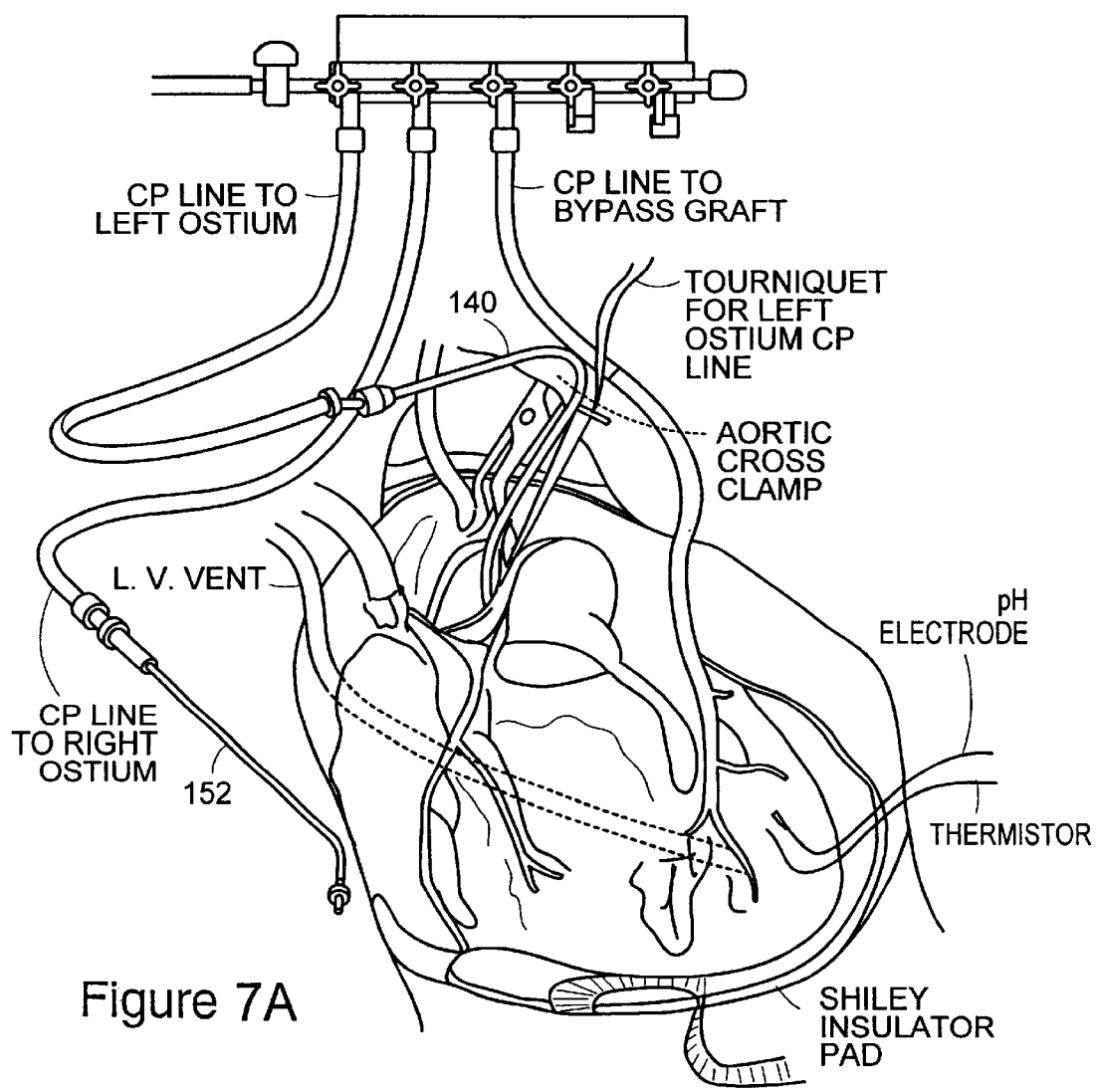
FIG. 7A shows a manifold cardioplegia delivery system and tools attached to a heart.
Figure 7B:
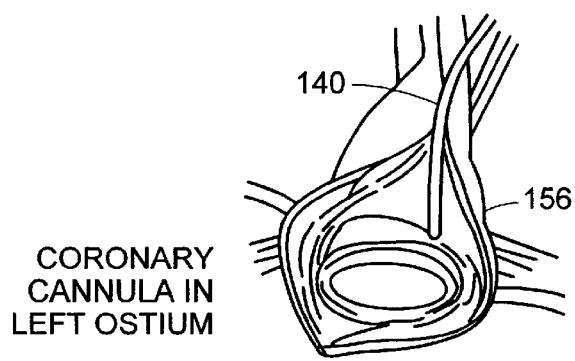
FIG. 7B shows a cannula placed within the left main coronary artery of the heart.

FIG. 6 illustrates a "turkey foot" cardioplegia delivery system 140 (Medtronic, Grand Rapids, Mich.). The delivery system 140 in conjunction with the electrode can form a myocardial management system. The system 140 can also include a data processing system 160, such as a computer, and a controller 158. The data processing system 160 can be programmed to receive measured data 162, such as the status of the patient and changes in system status. The data processing system 160 can be attached to a fluid source or fluid delivery system 144. The data processing system 160 can also be attached to the fluid source through the controller 158. The controller 158 can operate the fluid delivery system. The controller 158 can control the flow rate of a preservation fluid or cardioplegia fluid delivered to a surgical site. The controller 158 can also control the temperature of a preservation solution and a delivery site of a preservation solution. The system 140 has a plurality of controls 142 which can be used to adjust and selectively administer the amount of cardioplegia solution delivered from a source 144 to various cardiac attachment sites. The system 140 can include an occluder or valve 146 which controls the flow of the cardioplegic solution. The system 140 includes several delivery devices attached between the cardioplegia source 144 and various cardiac sites. These devices allow the delivery of cardioplegic solution to their respective cardiac sites. One device is a cannula 148 (Sarns Inc., Ann Arbor, Mich.) which can be inserted in the aortic root. Another device is a Spencer cannula 150 (Research Medical, Inc., Midvale, Utah) which can be inserted within the orifice 156 of the left main coronary artery. This insertion into the orifice 156 is shown in FIGS. 7A and 7B. Another device is a malleable metallic catheter 152 (Medtronic, Grand Rapids, Mich.) which can be inserted within the orifice of the right main coronary artery. The catheter 152 is also shown in FIG. 7A in an uninserted state. Another device is a 14 gauge beaded needle (Randall Faichney Corp., Avon, Mass.) which can be attached to the proximal end of a saphenous vein graft for the delivery of cardioplegia. The attachment to the vein graft is also shown in FIG. 7A.

Blocking the orifice of the left main coronary ostium with a spherical catheter such as a Spencer cannula 150 (Research Medical, Inc., Midvale Utah) or balloon tipped catheter such as a #3F Fogerty Catheter (Ideas For Medicine, St. Petersburg, Fla.), while providing cardioplegia through other sites of 140, can also be used to redistribute cardioplegia solution during cardiac surgery. Also, applying temporary occlusive pressure to a coronary artery proximal to the site of insertion of a new vein graft while perfusing a cardioplegic solution through the proximal end of the graft can also be used to re-direct cardioplegic fluid during cardiac surgery. Occlusive pressure can be maintained with a gauze "peanut" at the tip of a Kelly clamp (Allegiance Healthcare Corp., McGaw Park, Ill.).

Figure 8:
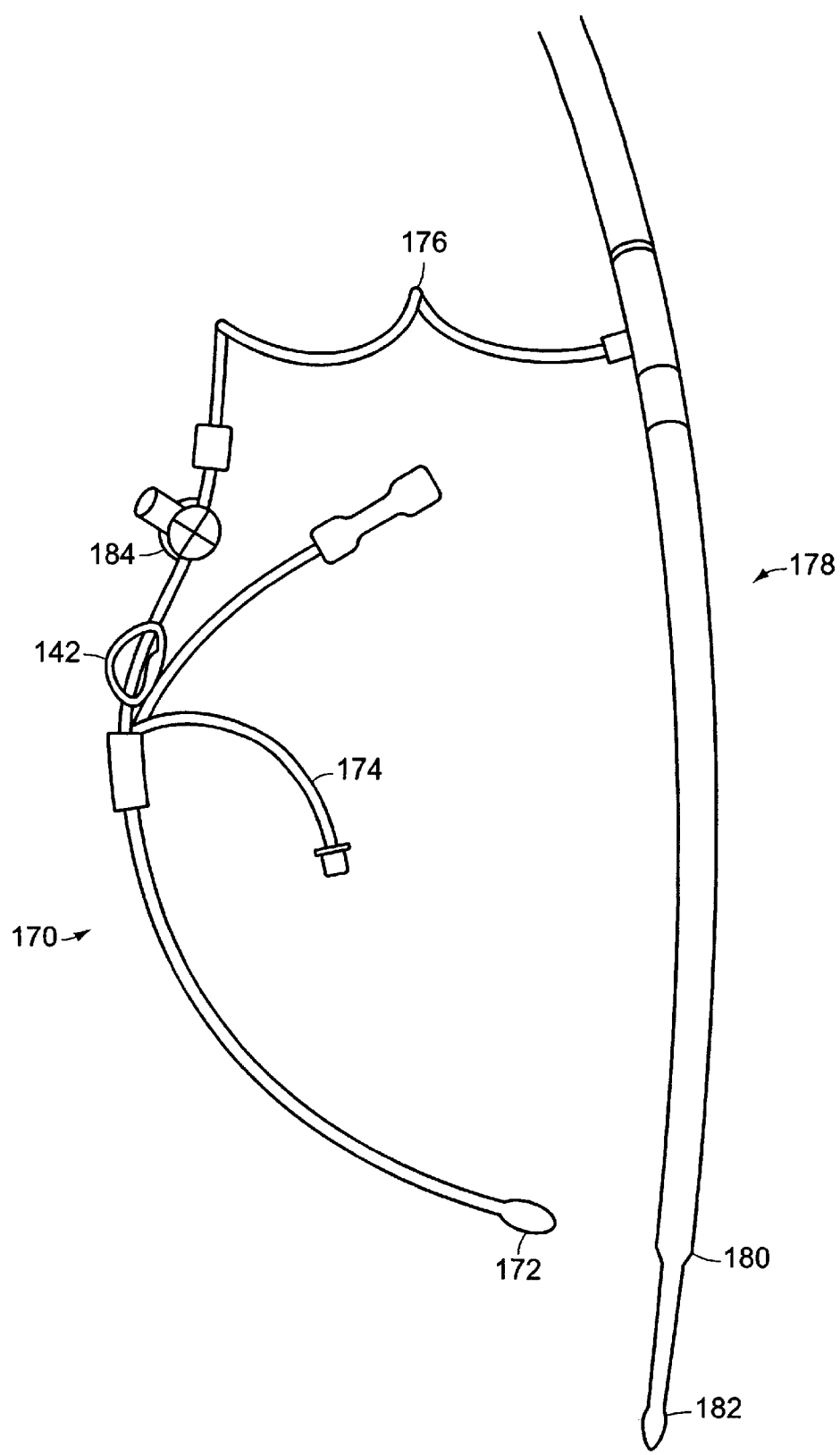
FIG. 8 shows a coronary sinus cannula connected to a venous cannula.

A Guntrie balloon tipped cannula (Medtronic, Grand Rapids, Mich.) can also be attached to the system 140 and inserted in the coronary sinus for selective administration of cardioplegia in a retrograde manner. The cannula 170 is illustrated in FIG. 8. In this figure, it is illustrated attached through tubing 176 to the venous cannula 178. This allows manipulating the pressure in the coronary sinus to improve cardioplegia delivery to the tissues as part of pH-guided myocardial management. The pressure can be manipulated by inflating a coronary sinus balloon 172 with the fluid orifice of the coronary sinus catheter closed, and delivering the cardioplegia antegrade. The 1 mm tubing 176 connecting 170 to 178 creates back pressure which will improve delivery without interfering with adequate antegrade cardioplegia flows. The opening or closing of the fluid orifice of the coronary sinus catheter 170 can be controlled by a valve 184. The venous cannula 178 is normally inserted in the course of cardiopulmonary bypass with its tip 182 in the inferior vena cava and its more proximal orifice 180 in the right atrium.

Changing the tissue temperature by manipulating the temperature of the cardioplegic solution using a water heater/cooler, such as that manufactured by Sarns, Ann Arbor, Mich., can aid in managing myocardial pH during cardiac surgery.

Also, changing the perfusion pressure of the cardioplegic solution by changing the rate of cardioplegia flow using a cardioplegia system such as an HE30 Gold cardioplegia system (Baxter Corporation, Irvine, Calif.) can aid in managing myocardial pH during cardiac surgery.

Tools can also be used for the assessment of myocardial viability and the determination of the physiologic significance of coronary stenosis. The tools can be used in either an operating room or a cardiac catheterization lab.

In the operating room, pacing wires (Ethicon, Somerville, N.J.) can be placed over the right atrium and connected to an external pacemaker (Medtronic, Grand Rapids, Mich.). A pH electrode can also be inserted into the myocardium. A fall in myocardial pH in response to 5 minutes of rapid atrial pacing can indicate tissue ischemia and also can indicate that the myocardial segment in which the electrode is placed is viable.

In the cardiac catheterization laboratory, the pH electrode can be mounted at the tip of a long 0.014 gauge wire and inserted through a regular 6 french cardiac catheterization catheter such as that manufactured by Cordis (Miami, Fla.). The catheter tip can be positioned perpendicularly against the ventricular wall of the segment subtended by the coronary artery being investigated and the pH electrode pushed to penetrate into the subendocardium. Preferably, the electrode is pushed to penetrate 5 mm into the subendo cardium. Pacing is achieved via a pacing wire advanced into the right ventricle (Medtronic, Grand Rapids, Mich.) and attached to an external pacemaker (Medtronic, Grand Rapids, Mich.). Again, a fall in myocardial pH in response to 5 minutes of rapid arterial pacing can indicate tissue ischemia.

While the pH electrodes and monitoring system have been described for use in determining the ischemia of cardiac tissue, the pH system and methods can be used in other types tissue as well. The pH system can be used to monitor rejection in organ transplantation, to assess mesenteric ischemia, to monitor and assess brain blood flow and to monitor flaps in plastic surgery.

The pH electrode can be used to monitor the kidney in the course of and following kidney transplantation. The pH electrode can be used in the monitoring of tissue perfusion to the kidney in the course of major surgery and, in particular, during kidney transplantation. The electrode is readily implantable in the kidney in a manner similar to the heart, and a tissue pH level of 7.2 and above indicates adequate tissue perfusion. Damage to the kidney, particularly during excision of the kidney for the purpose of donor related cardiac transplantation, can be detected and avoided, thus insuring a better outcome of the donor related kidney transplantation. Preservation of the kidney during transport prior to transplantation can also be insured by monitoring and maintaining the pH at normal levels. This can be achieved with constant perfusion of the kidney with blood in a specially designed apparatus for organ perfusion.

Following kidney transplantation, keeping the electrode in the kidney throughout the immediate 48 hours postoperatively can allow for monitoring initial ischemia and can allow for reversing of this ischemia with operative interventions. Ischemia during this period can herald a significant bad outcome. Assessment of the transplanted kidney, function and detection of its rejection can also be performed by placing the electrode on a catheter and passing it retrograde into the calyx of the kidney. Puncturing the calyx of the kidney along with the kidney parenchyma, similar to what was described above for the heart, can indicate impending or actual rejection and, as such, would be indicative of adverse outcome. Early detection of acidosis can prompt major treatment of rejection, and thus can improve the outcome of kidney transplantation.

Each electrode can be used also for the assessment of the adequacy of the revascularization of the kidney in the course of renal artery revascularization. The efficacy of the revascularization of a critically stenod renal artery can be determined intra-operatively in a manner similar to the efficacy of the revascularization of the coronary arteries. Failure to reverse acidosis with revascularization should prompt additional intra-operative measures to reverse the acidosis, and hence, avoid adverse outcome of revascularization. As in the heart, failure to reverse the acidosis with revascularization is indicative of the inadequacy of the revascularization process and provides a guide for additional intra-operative management to improve the situation and improve the outcome of the revascularization.

The pH electrode can also be used to monitor the liver during and following liver transplantation. The pH electrode can be inserted into the liver to provide important data similar to that of the kidney, described above. The description of the use of the electrode in the kidney is applicable to the liver in terms of the use of the pH electrode in monitoring the intra-operative course, identifying early rejection, and instituting measures to reverse the rejection process.

The electrode can also be used in monitoring the periphery in critical care. Insertion of the electrode in the subcutaneous tissue of the periphery should provide information on the adequacy of tissue perfusion. Acidosis measured at these sites, primarily in the subcutaneous tissue of the distal half of the lower extremity, can indicate an inadequate cardiac output, and can prompt the institution of measures to improve cardiac output or tissue perfusion. These measures can include pharmacologic manipulations and/or insertion of an intra-aortic balloon (Arrow International, Reading, Penn.) in the descending aorta, for example. Currently, only measures of central hemodynamics are used to assess and treat low cardiac output syndrome. Measuring the pH in the periphery provides a more superior alternative because it provides a true measure of tissue perfusion which is the ultimate goal in the maintenance of an "adequate" cardiac output.

The electrode can also be used within the muscle and subcutaneous tissue of flaps in plastic surgery. It has been demonstrated that tissue acidosis with the pH electrode indicates compromised viability of skin and subcutaneous flaps. The electrode is placed post-operatively within the edge of the flap and the pH is monitored up to three or four days post-operatively. A fall in pH prompts an intra-operative intervention and a revision of the flap to prevent its subsequent failure.

The pH electrode can also be used in the colon in the assessment and treatment of intestinal ischemia. To assess and reverse intestinal ischemia, the pH electrode can be placed on a wire in a manner similar to that described for the heart during cardiac catheterization above. This pH electrode-tipped wire can be inserted through a colonoscope, such as that manufactured by Olympus Medical, Seattle, Wash., during regular colonoscopy into the distal ileum. Intra-luminal pH in the ilium is a reliable measure of the adequacy of the perfusion. Intra-luminal acidosis in the ilium indicates intestinal ischemia, and can prompt maneuvers to either reverse the ischemia or to prevent its adverse outcome. Knowledge of intra-luminal pH in the ilium allows the initiation of operative interventions, such as exploration of the abdomen with the possible resection of intestine for example, as well as pharmacologic interventions to improve cardiac output and tissue perfusion.

The pH electrode can be used in other organs. In addition to the organs mentioned above, tissue acidosis can be measured, manipulated, and reversed by inserting the pH electrode, attached to the pH monitoring system, in organs such as the brain, the bladder, the diaphragm, and the small intestine.

Acidosis can prematurely trigger and accelerate cell apoptosis, or programmed cell death. In the heart, apoptosis may manifest in late adverse outcomes, mainly progressive heart failure. During the course of open heart surgery, moderate to severe acidosis is encountered, at least in one segment of the left ventricle, in more than 50% of the patients. The prevention of the onset of myocardial tissue acidosis by pH-guided myocardial management in the course of open heart surgery reduces or eliminates the potential of triggering apoptosis, and hence reduce or eliminate the potential of late adverse postoperative outcomes.

While this invention has been particularly shown and described with references to preferred embodiments thereof, it will be understood by those skilled in the art that various changes in form and details may be made therein without departing from the scope of the invention encompassed by the appended claims.

What is claimed is:

1. A tissue monitoring system comprising:
   a pH electrode for insertion into tissue at a site; and
   a fluid delivery system having a manifold connected to a fluid source to control fluid flow to a plurality of sites and having a valve, the system including a probe to be inserted at least at one of the plurality of sites.

2. The system of claim 1 wherein the pH electrode is adapted to contact tissue of a patient such that pH data of the tissue is monitored to determine if tissue pH deviates from a threshold level indicative of ischemia.

3. The system of claim 1 further comprising a data processor and a controller that is connected to the fluid delivery system.

4. The system of claim 3 wherein the controller controls the flow rate of a preservation solution delivered to a surgical site.

5. The system of claim 3 wherein the controller controls temperature of a preservation solution.

6. The system of claim 3 wherein the controller controls a site of delivery of a preservation solution.

7. The system of claim 1 further comprising a catheter which delivers the fluid.

8. The system of claim 1 further comprising a temperature sensor that measures temperature of the tissue.

9. The system of claim 1 wherein the delivery system applies coronary artery pressure on a proximal portion of an artery.

10. The system of claim 1 further comprising a balloon catheter.

11. The system of claim 1 further comprising a balloon of a retrograde coronary sinus catheter.

12. The system of claim 1 wherein the pH electrode is positioned relative to cardiac tissue of a patient with a percutaneous catheter.

13. The system of claim 1 wherein the pH electrode is delivered to a tissue site of a patient using a laparoscope.

14. The system of claim 1 wherein the pH electrode is positioned using an endoscope.

15. A tissue monitoring system comprising:
- a pH electrode for insertion into tissue at a site;
- a temperature sensor that measures temperature of the tissue;
- a processor that determines tissue pH in response to a pH electrode measurement and a temperature measurement; and
- a fluid delivery system having a manifold connected to a fluid source to control fluid delivery to a plurality of sites and having a probe to be inserted into at least one site.

16. The system of claim 15 wherein the pH electrode is adapted to contact tissue of a patient such that pH data of the tissue is monitored to determine if tissue pH deviates from a threshold level indicative of ischemia.

17. The system of claim 15 further comprising a controller that is connected to the fluid delivery system.

18. The system of claim 17 wherein the controller controls the flow rate of a preservation solution delivered to a surgical site.

19. The system of claim 17 wherein the controller controls temperature of a preservation solution..

20. The system of claim 17 wherein the controller controls a site of delivery of a preservation solution.

21. The system of claim 15 further comprising a catheter which delivers the fluid.

22. The system of claim 15 the delivery system applies coronary artery pressure on a proximal portion of an artery.

23. The system of claim 15 further comprising a balloon catheter.

24. The system of claim 15 further comprising a balloon of a retrograde coronary sinus catheter.

25. The system of claim 15 wherein the pH electrode is positioned relative to cardiac tissue of a patient with a percutaneous catheter.

26. The system of claim 15 wherein the pH electrode is delivered to a tissue site of a patient using a laparoscope.

27. The system of claim 15 wherein the pH electrode is positioned using an endoscope.

* * * * *

UNITED STATES PATENT AND TRADEMARK OFFICE
CERTIFICATE OF CORRECTION

PATENT NO. : 6,600,941 B1
DATED : July 29, 2003
INVENTOR(S) : Shukri F. Khuri and Patrick Treanor It is certified that error appears in the above-identified patent and that said Letters Patent is hereby corrected as shown below:

<u>Title page,</u>
Item [75], please delete the inventor "Shukri F. Khuri, Westwood, MA (US)", and replace with -- Shukri F. Khuri, Westwood, MA (US) and Patrick Treanor, Dedham, MA (US) --.

<u>Column 16,</u>
Line 10, please delete "The system of claim 15 the delivery system applies" and insert -- The system of claim 15 wherein the delivery system applies --.

Signed and Sealed this

Thirteenth Day of January, 2004

JON W. DUDAS
*Acting Director of the United States Patent and Trademark Office*